US010572626B2

(12) United States Patent
Balram (10) Patent No.: US 10,572,626 B2
(45) Date of Patent: Feb. 25, 2020

(54) ADVANCED TELEMEDICINE SYSTEM WITH VIRTUAL DOCTOR

(71) Applicant: Nikhil Balram, Mountain View, CA (US)

(72) Inventor: Nikhil Balram, Mountain View, CA (US)

(73) Assignee: Ricoh Co., Ltd., Tokyo (JP)

(*) Notice: Subject to any disclaimer, the term of this patent is extended or adjusted under 35 U.S.C. 154(b) by 579 days.

(21) Appl. No.: 15/061,299

(22) Filed: Mar. 4, 2016

(65) Prior Publication Data

US 2017/0098051 A1    Apr. 6, 2017

Related U.S. Application Data

(60) Provisional application No. 62/237,722, filed on Oct. 6, 2015, provisional application No. 62/237,549, filed on Oct. 5, 2015.

(51) Int. Cl.
*G06F 19/00* (2018.01)
*G16H 10/60* (2018.01)

(52) U.S. Cl.
CPC ........ *G06F 19/3418* (2013.01); *G06F 19/325* (2013.01); *G16H 10/60* (2018.01)

(58) Field of Classification Search
None
See application file for complete search history.

(56) References Cited

U.S. PATENT DOCUMENTS

| 7,590,550 B2* | 9/2009 | Schoenberg ..... G06Q 10/06375 705/2 |
| 2007/0050715 A1* | 3/2007 | Behar .................. A61B 5/0002 715/706 |

(Continued)

FOREIGN PATENT DOCUMENTS

| WO | WO0070529 | 11/2000 |
| WO | WO0150330 | 7/2001 |
| WO | WO2013166146 | 11/2013 |

OTHER PUBLICATIONS

European Search and Written Report for EP Application EP16191633 dated Jan. 9, 2017, 9 pages.

(Continued)

*Primary Examiner* — Michael Tomaszewski
*Assistant Examiner* — Jay M. Patel
(74) *Attorney, Agent, or Firm* — Patent Law Works LLP (57) ABSTRACT

A telemedicine system with intelligent triage that replaces a remote doctor with a virtual doctor in some cases is disclosed. The telemedicine system may include: a triage procedure that employs a local attendant and software to determine if the patient should be seen by a human doctor or can be satisfactorily served by the virtual doctor AI system—the triage process is done at the start and throughout the consultation to ensure that the patient is handled appropriately, with several exit options for care to be provided by a human doctor if warranted; an AI system (e.g., an expert or knowledge-based system) comprising a knowledge-base, an inference engine, input module, output module, central/monitoring module, and learning module; and a remote control or operations center where the operation of the virtual doctors can be monitored by a set of human doctors who can choose to intervene if/when necessary.

20 Claims, 4 Drawing Sheets

(56) References Cited

U.S. PATENT DOCUMENTS

| | | | | |
|---|---|---|---|---|
| 2010/0121156 | A1* | 5/2010 | Yoo | G06F 19/3418 600/300 |
| 2010/0324936 | A1* | 12/2010 | Vishnubhatla | G06F 19/328 705/3 |
| 2011/0213625 | A1* | 9/2011 | Joao | G06F 19/328 705/3 |
| 2011/0224998 | A1* | 9/2011 | Schoenberg | G06Q 10/10 705/1.1 |
| 2012/0005030 | A1* | 1/2012 | Valin | G06Q 20/10 705/14.73 |
| 2012/0035959 | A1* | 2/2012 | Berdia | G06F 19/325 705/3 |
| 2012/0102199 | A1* | 4/2012 | Hopmann | G06F 9/5044 709/226 |
| 2012/0209394 | A1* | 8/2012 | Bojarski | A61F 2/30942 623/20.32 |
| 2013/0024209 | A1* | 1/2013 | Goldenberg | G06F 19/324 705/3 |
| 2013/0060576 | A1* | 3/2013 | Hamm | G06F 19/3418 705/2 |
| 2013/0138455 | A1* | 5/2013 | Saharan | G06Q 50/22 705/2 |
| 2014/0019149 | A1* | 1/2014 | Yu | G16H 80/00 705/2 |
| 2015/0019241 | A1* | 1/2015 | Bennett | G16H 50/00 705/2 |
| 2015/0142466 | A1* | 5/2015 | Macoviak | G06F 19/328 705/2 |
| 2015/0161331 | A1* | 6/2015 | Oleynik | G16H 10/60 705/3 |
| 2016/0188799 | A1* | 6/2016 | Borras | G06F 19/321 705/3 |

OTHER PUBLICATIONS

United Nations "Africa Faces 'dramatic' physician shortage by 2015, cautions UN health agency" dated Jul. 2, 2002, 1 page.
Dehn, Richard W. MPA, PA-C "Global Physician Shortages and the PA Profession" dated Oct. 2008, 3 pages, JAAPA Oct. 2008.
Anonymous Physician Shortage Projected to Soar to More than 91,000 in a Decade dated Oct. 11, 2010, 2 pages, American Medical News.
Pauline W. Chen "Where Have All the Primary Care Doctors Gone?" dated Dec. 20, 2012, 3 pages, The New York Times.
Anonymous "Doctor Shortage Reaching Crisis, Study Warns" dated Sep. 3, 2016, 2 pages, The Local Germany.
Tehrani et al., "Wearable Technology and Wearable Devices Everything You Need to Know—Introduction to Wearable Technology," Mar. 26, 2014, XP055501079, WearableDevices.com, retrieved from http://www.wearabledevices.com/what-is-a-wearable-device/ on Aug. 21, 2018, 2 pgs.

* cited by examiner

ADVANCED TELEMEDICINE SYSTEM WITH VIRTUAL DOCTOR

CROSS REFERENCE TO RELATED APPLICATIONS

The present application claims priority, under 35 U.S.C. § 119, of U.S. Provisional Patent Application No. 62/237,722, filed Oct. 6, 2015 and entitled "Advanced Telemedicine System with Virtual Doctor," and U.S. Provisional Patent Application No. 62/237,549, filed Oct. 5, 2015 and entitled "Advanced Telemedicine System with Virtual Doctor," which are incorporated by reference in its entirety.

BACKGROUND

In many parts of the world, the provision of adequate healthcare has been complicated due to the lack of sufficient number of doctors located in proximity to the patients. Advanced digital/mobile technology providing low cost connectivity and compute power has enabled the option of large scale telemedicine and advanced cloud-based systems are being deployed. These systems enable a variety of care to be delivered to patients conveniently and cost-effectively using local systems and attendants and remote doctors using video conferencing.

The current focus has been on expanding the deployment of these systems and attracting a large flow of patients (the demand side). There has not been much attention given to the supply side—the fact that qualified and competent doctors are in short supply in most parts of the world and the remote doctor is the most expensive element of the system, typically 30-60% of the cost of a consultation—both these issues are big barriers to achieving very large scale deployment of telemedicine.

SUMMARY

Systems and methods for a telemedicine system with intelligent triage are disclosed. For example, in some implementations, the telemedicine system may receive a registration of a patient at a node. The telemedicine system may then receive an input regarding the patient and determine, using the input, whether the patient can be treated by a virtual doctor. In response to determining that the patient can be treated by the virtual doctor, the telemedicine system may provide a treatment decision for the patient, using an inference engine and a knowledge base of the virtual doctor, based on the input.

Other implementations of one or more of these aspects include corresponding systems, apparatus, methods, and computer programs, configured to perform the actions of the methods, encoded on computer storage devices. It should be understood that the above is not all-inclusive and many additional steps, features and advantages are contemplated and fall within the scope of the present disclosure. Moreover, it should be understood that the language used in the present disclosure has been principally selected for readability and instructional purposes, and not to limit the scope of the subject matter disclosed herein.

BRIEF DESCRIPTION OF THE DRAWINGS

The embodiments are illustrated by way of example, and not by way of limitation in the figures of the accompanying drawings in which like reference numerals are used to refer to similar elements.

DETAILED DESCRIPTION

A system and method for treating a patient using an advanced telemedicine system with a virtual doctor is described. In the following description, for purposes of explanation, numerous specific details are set forth in order to provide a thorough understanding of the embodiments. It will be apparent, however, to one skilled in the art that the embodiments can be practiced without these specific details. In other instances, structures and devices are shown in block diagram form in order to avoid obscuring the embodiments. For example, one embodiment is described below with reference to user interfaces and particular hardware. However, the present embodiments apply to any type of computing device that can receive data and commands, and any peripheral devices providing services.

Reference in the specification to "one embodiment" or "an embodiment" means that a particular feature, structure, or characteristic described in connection with the embodiment is included in at least one embodiment. The appearances of the phrase "in one embodiment" in various places in the specification are not necessarily all referring to the same embodiment.

Some portions of the detailed descriptions that follow are presented in terms of algorithms implemented as operations on data bits within a computer memory. These algorithmic descriptions are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms including, for example, processing, computing, calculating, determining, displaying, or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present embodiments also relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, including, but not limited to, any type of disk including floppy disks, optical disks, CD-ROMs, and magnetic disks, read-only memories (ROMs), random access memories (RAMs), EPROMs, EEPROMs, magnetic or optical cards, flash memories or any type of media suitable for storing electronic instructions.

The embodiments can take the form of an entirely hardware embodiment, an entirely software embodiment or an embodiment containing both hardware and software elements. An example embodiment is implemented in software, which includes but is not limited to firmware, resident software, microcode, etc.

Furthermore, the embodiments can take the form of a computer program product accessible from a non-transitory computer-usable or computer-readable medium providing program code for use by or in connection with a computer or any instruction execution system. For the purposes of this description, a computer-usable or computer readable medium can be any apparatus that can contain, store, or transport the program for use by or in connection with the instruction execution system, apparatus, or device.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

Finally, the algorithms and displays presented herein are not inherently related to any particular computer or other apparatus. Various general-purpose systems may be used with programs in accordance with the teachings herein, or it may prove convenient to construct more specialized apparatus to perform the method steps. In addition, the present embodiments are not described with reference to any particular programming language. It will be appreciated that a variety of programming languages may be used to implement the teachings of the embodiments as described herein.

The techniques and systems disclosed herein overcome the deficiencies of the prior art by providing a telemedicine system with intelligent triage that replaces the remote doctor with a virtual doctor in the majority of cases where the circumstances are conducive to satisfactory handling by an artificial intelligence system (e.g., an expert system or knowledge-based system). The telemedicine system may include a triage procedure at the tele-clinic that employs a local attendant and software to determine if the patient needs to be seen by a human doctor or can be satisfactorily served by the virtual doctor AI system. The triage process is done at the start and throughout the consultation to ensure that the patient is handled appropriately, with several exit options to review by a human doctor if warranted. The telemedicine system may further include an AI system (e.g., an expert or knowledge-based system) comprising a knowledge-base, an inference engine, input module, output module, central/monitoring module, and learning module. In some embodiments, the telemedicine system includes a remote control or operations center where the operation of the virtual doctors can be monitored by a set of human doctors who can choose to intervene if/when necessary. The control or operations centers could be large control/operation centers or distributed centers with individual doctors operating in their own locations with a set of consultations being shown/shared with them on an individual dashboard.

The same principles of leverage using triage with AI could be applied to other types of medical professionals like nurse practitioners/physicians assistants (e.g., expanding virtual doctor to virtual healthcare professional and various specialty care options that have well-defined workflows). Major advantages of the system are significantly higher availability of care at significantly lower cost. Additional advantages over existing telemedicine systems include an increased number of patients that may be seen, particularly for minor healthcare issues, since a large portion of routine cases can be handled by a virtual doctor. Further, a small team of physicians may monitor a relatively large number of virtual doctor sessions to intervene if an exception is noted (either by the virtual doctor or a monitoring physician). Thus, applying the techniques and systems described herein, more patients can be seen with fewer resources than in existing telehealth systems.

Figure 1:
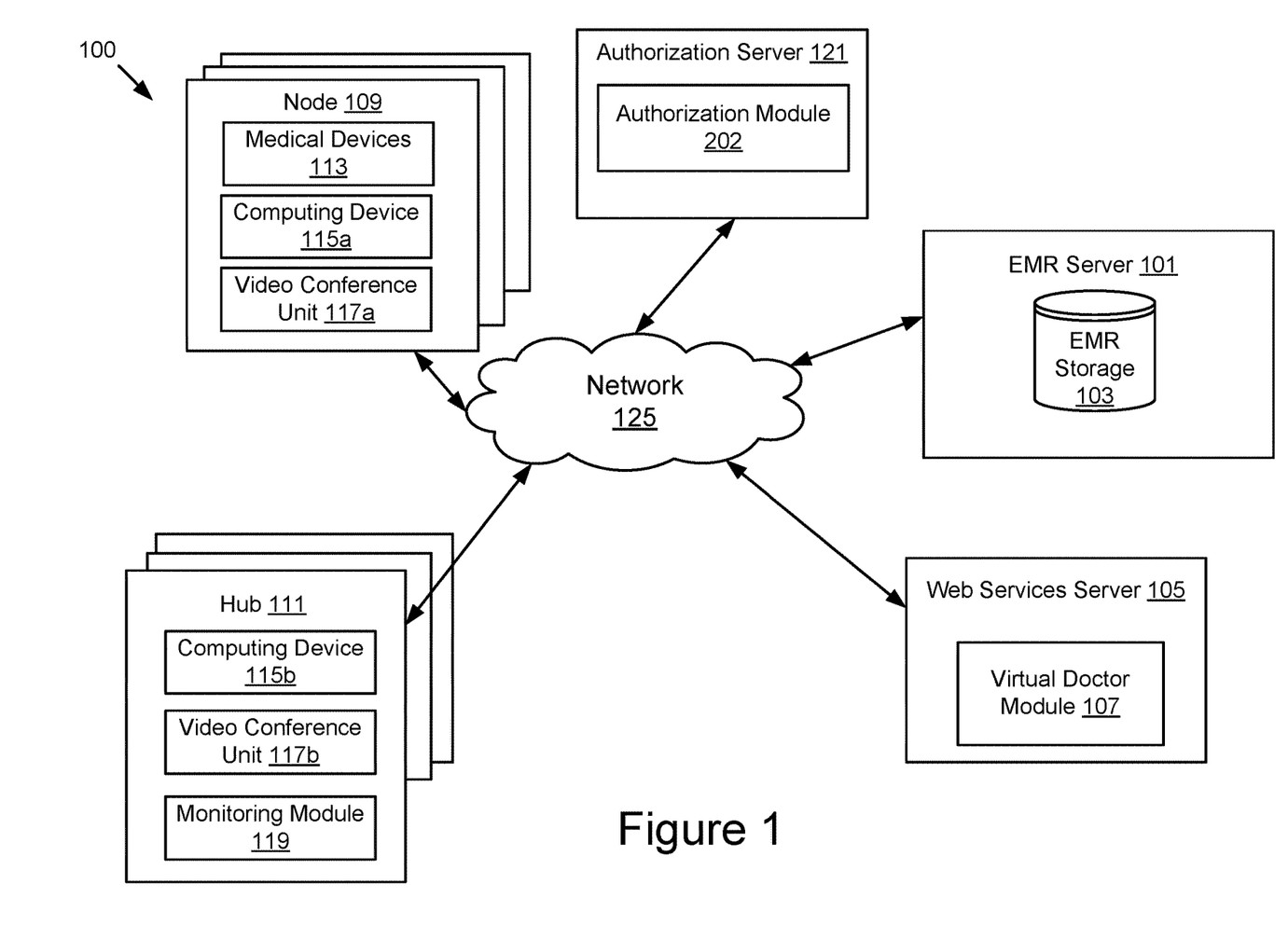
FIG. 1 illustrates a block diagram of an advanced telemedicine system according to one embodiment.

FIG. 1 illustrates a block diagram of an advanced telemedicine system 100 according to one embodiment. The illustrated system 100 includes one or more nodes 109, an authorization server 121, an electronic medical record (EMR) server 101, one or more hubs 111, and a web services server 105. In the illustrated embodiment, these entities are communicatively coupled via a network 125.

While FIG. 1 illustrates three nodes 109 and three hubs 111, the techniques introduced herein may be implemented on any system architecture having one or more nodes 109 and one or more hubs 111. Additionally, while the example of FIG. 1 illustrates only one network 125 coupling the nodes 109, the hubs 111, the EMR server 101 and the web services server 105, in practice any number of networks 125 can be used to connect the entities. Furthermore, although only one EMR server 101 is shown, it will be recognized that multiple EMR servers 101 may be present. Moreover, although only one web services server 105 is shown, it will be recognized that multiple web services servers 105 may be present.

In one embodiment, the authorization server 121 comprises an authorization module 202 and is connected to the network 125. The authorization module 202 is code and/or routines for registering a user and generating a token for a user. In one embodiment, the authorization module 202 is a set of instructions executable by a processor. In another embodiment, the authorization module 202 is stored in memory and is accessible and executable by the processor.

The authorization module 202 serves as a gatekeeper for managing user access to the EMR server 101 and the web services server 105. In one embodiment, the authorization module 202 registers users including one or more of a medical service provider, node personnel, and a patient. In one embodiment, the authorization module 202 registers medical service providers. In one embodiment, registering a medical service provider includes medical service provider login. For example, the authorization module 202 may register a medical service provider when the authorization module 202 receives, from the hub 111, a login request associated with a medical service provider and determines to allow the login. In one embodiment, registering a medical service provider includes maintaining a medical service provider account. For example, in one embodiment, the authorization module 202 manages medical service provider accounts by creating medical service provider accounts (e.g., when new medical service providers are added to the system 100) and by updating existing medical service provider accounts. In one embodiment, a medical service provider account includes information regarding one or more of the associated medical service provider's education, experience and medical specialty.

In one embodiment, the authorization module 202 registers node personnel. In one embodiment, registering node personnel includes node personnel login. For example, in one embodiment, the authorization module 202 registers a technician when the authorization module 202 receives, from the node 109, a login request associated with the technician and determines to allow the login. In one embodiment, registering node personnel includes maintaining a node personnel account. For example, in one embodiment, the authorization module 202 manages node personnel accounts by creating node personnel accounts (e.g., when new node personnel are added to the system 100) and by updating existing node personnel accounts.

In one embodiment, the authorization module 202 registers patients. In one embodiment, registering a patient includes using a virtual doctor module 107 to triage and/or treat the patient. For example, assume a patient has arrived at the node 109 seeking a medical consultation, in one embodiment, the authorization module 202 registers the patient by passing a patient check-in signal to the virtual doctor module 107 and the virtual doctor module 107 determines how to treat the patient. In one embodiment, registering a patient includes patient intake. For example, assume a patient has arrived at the node 109 seeking a medical consultation, in one embodiment, the authorization module 202 registers the patient by requesting to update the patient's EMR in the EMR storage 103 or (if the patient is new) requesting to create a new EMR in the EMR storage 103. It will be recognized that the preceding are merely examples of registering patients and that other examples exist.

In one embodiment, the authorization module 202 registers users and issues a token to each user. For example, a nurse at the node 109 provides registration information, including for example a login/password or an authorized certificate, and the authorization module 202 issues a token for the nurse. In some embodiments, the EMR server 101 generates the token and the authorization module 202 uses the token to verify the identity of the user before providing the user with access to the web services server 105. The token is used to identify a user's identity. The authentication process can be implemented as a sign-on process (e.g. a process that supports ID as a service) or over HTTPS.

FIG. 1 illustrates the authorization module 202 as being part of a sign-on server (the authentication server 121). In another embodiment, the authorization module 202 and its functionality are distributed across the system 100 (e.g. across the node 109, the hub 111, the EMR server 101 and the web services server 105). Distributing functionality in different servers is helpful in load balancing. In another embodiment, the authorization module 202 and its authorization functionality are included in the web services server 105.

In one embodiment, a virtual doctor module 107 is included in the web services server 105 and is operable on the web services server 105, which is connected to the network 125. In one embodiment, the virtual doctor module 107 includes multiple, distributed modules that cooperate with each other to perform the functions described below. Details describing the functionality and components of the virtual doctor module 107 are explained in further detail below with regard to FIGS. 2A, 2B, and 3.

The network 125 enables communications between the nodes 109, the EMR server 101, the hubs 111 and the web services server 105. Thus, the network 125 can include links using technologies including, for example, Wi-Fi, Wi-Max, 2G, Universal Mobile Telecommunications System (UMTS), 3G, Ethernet, 802.11, integrated services digital network (ISDN), digital subscriber line (DSL), asynchronous transfer mode (ATM), InfiniBand, PCI Express Advanced Switching, etc. Similarly, the networking protocols used on the network 125 can include the transmission control protocol/Internet protocol (TCP/IP), multi-protocol label switching (MPLS), the User Datagram Protocol (UDP), the hypertext transport protocol (HTTP), the simple mail transfer protocol (SMTP), the file transfer protocol (FTP), lightweight directory access protocol (LDAP), Code Division Multiple Access (CDMA), Wideband Code Division Multiple Access (WCDMA), Global System for Mobile communications (GSM), High-Speed Downlink Packet Access (HSDPA), etc. The data exchanged over the network 125 can be represented using technologies and/or formats including the hypertext markup language (HTML), the extensible markup language (XML), etc. In addition, all or some of links can be encrypted using conventional encryption technologies, for example, the secure sockets layer (SSL), Secure HTTP and/or virtual private networks (VPNs) or Internet Protocol security (IPsec). In another embodiment, the entities can use custom and/or dedicated data communications technologies instead of, or in addition to, the ones described above. Depending upon the embodiment, the network 125 can also include links to other networks.

In one embodiment, the network 125 is a partially public or a wholly public network, for example, the Internet. The network 125 can also be a private network or include one or more distinct or logical private networks (e.g., virtual private networks, Wide Area Networks (WAN) and/or Local Area Networks (LAN)). Additionally, the communication links to and from the network 125 can be wireline or wireless (i.e., terrestrial or satellite-based transceivers). In one embodiment, the network 125 is an IP-based wide or metropolitan area network.

In one embodiment, EMR server 101 includes EMR storage 103. In one embodiment, the EMR storage 103 is a database that includes electronic medical records for patients of the system 100. In one embodiment, each time a node 109 or hub 111 transmits information about a patient, the EMR storage 103 updates that patient's electronic medical record.

In one embodiment, the node 109 is where patients receive a medical consultation and includes a computing device 115a and various medical devices 113. In one embodiment, the node 109 is located remotely from the hubs 111. For example, the node 109 is a facility physically located in a rural area and a hub 111 is physically located in a city or other metropolitan area. In another example, the node 109 is a patient's home and the hub 111 is a nearby hospital. It will be recognized that the preceding are merely examples of a node 109 located remotely from a hub and that other examples exist. In one embodiment, the node 109 is mobile. For example, the node 109 is a vehicle with a computing device 115a and medical devices 113, which travels to various locations and patients receive medical consultations at the vehicle. Examples of medical devices 113 include, but are not limited to, a stethoscope, a blood pressure meter, a pulse oximeter, a thermometer, an opthalmoscope, a weight and height scale, an otoscope, a camera, a telecardiology device (e.g. an ECG machine), a telepathology device (e.g. a microscope), a teledermatology device (e.g. a high-resolution camera), a teleradiology device (e.g. an ultrasound machine), etc.

In one embodiment, one or more of the medical devices 113 are integrated with the node 109. In one embodiment, an integrated medical device is communicatively coupled to the node 109 to enable store and forward functionality. For example, in one embodiment, an integrated medical device 113 is communicatively coupled to the node's computing device 115a to automatically send its output to the computing device 115a. The integrated medical device output is captured by software on the node's computing device 115a and automatically forwarded to the EMR server 101 according to one embodiment. Such an embodiment may beneficially reduce errors from node personnel misreading the medical device 113 and transcription errors from node personnel miss-recording the output of the medical device 113.

Store and forward is an asynchronous, non-interactive form of telemedicine. In one embodiment, store and forward is applied when the patient and doctor are not available at the same time. For example, in one embodiment, patient data is collected or acquired by the node 109 and stored on a computing device 115a at the node 109, and then forwarded to a hub doctor via the network 125. The hub doctor, at a later time, reviews the information and responds with a diagnosis, recommendations, requests for additional information etc.

In some embodiments, the node 109 uses store and forward when there is no direct connectivity between the node 109 and the hub 111. The node 109 stores a local copy of the patient data and synchronizes with the hub 111 whenever the node 109 is connected to the network 125. This is particularly helpful in this situation because the node 109 can often experience poor network connections. For example, when a technician is out in a remote region helping patients, the technician can gather the patient data, wait until the node 109 has a better connection, sync up the data to the EMR server 101 and a notification will be sent to the appropriate doctor to view the case and perform a diagnosis. After receiving the diagnosis from the doctor, the technician can give out prescribed medicine or perform additional lab-work request for the patient.

In other embodiments, the virtual doctor module 107 may reside on the node 109 and the functionality of the virtual doctor as described herein may be implemented even when experiencing network conditions that would not be sufficient for a synchronous telemedicine session with a live doctor.

The node 109 is staffed by personnel to operate the computing device 115a and medical devices 113. For example, the personnel may be a nurse trained to use the medical devices 113 to obtain the patient's medical information and to use the computing device 115a to register the patient for medical consultation. In one embodiment, the personnel at the node 109 is not as highly educated and/or is less specialized than the medical service provider at the hub 111. For example, assume the node is staffed by one or more of a nurse, medical technician, lab technician, physician's assistant and the medical service provider is a doctor (e.g. a general practitioner or a specialist).

Staffing the node 109 with personnel that are not medical service providers may beneficially increase the effectiveness of each medical service provider in the system 100. For example, where there is a shortage of doctors in the region, each remote node 109 includes a medical technician, who may be trained more quickly than a doctor. In one embodiment, the medical technician registers the patient, takes the patient's vital signs and uses additional medical devices 113 based on the complaint. Further, the node personnel may treat the patient for conditions not requiring care from a doctor. The doctor receives the medical information of the patient, which was gathered in part by the medical technician, and consults with the patient. For example, if the patient is complaining about a rash, the technician may use the high-resolution camera to take a picture of the problematic area, which the doctor may view and discuss with the patient. The doctor's effectiveness is therefore increased by allowing the medical service provider to spend more time consulting with and diagnosing patients and less time traveling to the various, remote locations of patients and performing less specialized tasks such as patient registration, gathering basic vital signs, etc.

The node 109 includes at least one computing device 115a. In one embodiment, the computing device 115a is used by a patient at the node to access a medical service provider at the hub 111 for medical consultation. For example, the computing device 115a is a laptop computer, a desktop computer, a tablet computer, a mobile telephone, a personal digital assistant (PDA), a mobile email device, a television with one or more processors embedded therein or coupled thereto or any other electronic device capable of accessing the network 125.

In one embodiment, the node 109 includes a video conference unit 117a. In one embodiment, the video conference unit 117a is a hardware based solution. In another embodiment, the video conference unit 117a is a software based solution. In one embodiment, the video conference unit 117a is a computing device 115a including a web camera or other device for capturing video of the patient and video conferencing software. Regardless of the embodiment, the video of the patient is transmitted to the hub 111 after a telemedicine session with a live doctor is initiated. The video conference unit 117a used by a patient at the node 109 to access a medical service provider at the hub 111 for medical consultation is occasionally referred to herein as a consultation device.

In various embodiments, a hub 111 may be any location a physician or other medical service provider (e.g., nurse practitioner, physician's assistant, or the like) connects to the advanced telemedicine system. For example, the hub 111 may be a doctor's office, hospital, other healthcare facility, a physician's home, or the like. In other embodiments, the hub 111 may be a remote operations center where a team of doctors may monitor one or more patients connected to the telemedicine system. In one embodiment, the remote operations center may be an intensivist hub where specially trained intensive care doctors monitor and consult with physicians and/or patients at a node 109 to treat patients with critical healthcare issues. The hub 111 connects with the nodes 109 and allows a medical service provider to remotely consult with and diagnose patients at a node 109 on an as needed basis using an information technology infrastructure (not shown). The hub's 111 information technology infrastructure includes, for example, a computing device 115b, a video conference unit 117b, a monitoring module 119, a digital clipboard, a monitor, a collaboration display and a printer. The monitoring module 119 allows a physician or other medical service provider to monitor the operations of the virtual doctor module 107 and intervene if the situation should warrant a telemedicine session with a live doctor.

The hub 111 includes at least one computing device 115b. In one embodiment, the computing device 115b is used by the medical service provider at the hub 111 to access patient information and consult with a patient at the node 109. For example, the computing device 115b is a laptop computer, a desktop computer, a tablet computer, a mobile telephone, a personal digital assistant (PDA), a mobile email device, a television with one or more processors embedded therein or coupled thereto or any other electronic device capable of accessing the network 125. The hub 111 includes software, for example, that allows doctors to log into the system, search for patients, schedule patients, order prescriptions, make notes, perform video conferencing, generate reports and perform analytics, and monitor virtual doctor sessions.

In one embodiment, the hub 111 includes a video conference unit 117b. In one embodiment, the video conference unit 117b is a hardware based solution. In another embodiment, the video conference device 117b is a software based solution. In one embodiment, the video conference unit is a computing device 115b including a web camera or other device for capturing video of the medical service provider and video conferencing software. Regardless of the embodiment, the video of the medical service provider is transmitted to the node 109 when the medical service provider is consulting with a patient at the node 109.

By allowing remote consultation of a patient at a node by a medical service provider at a hub, the medical service provider is more effectively used and patients may receive higher quality medical care. For example, assume the medical service provider is a cardiologist in a major city where the hub 111 is located. Also assume that a patient located in a rural location far from the city is having heart related problems. In one embodiment, the hub allows the cardiologist to remotely consult with and diagnose the rurally located patient without traveling to the patient's location. Therefore, the cardiologist may use the time the cardiologist would have spent traveling to the patient to consult with and diagnose additional patients thereby increasing the utilization of the cardiologist. Moreover, the rural patient is allowed to consult with and be diagnosed by a specialist (i.e. a cardiologist who specializes in the cardiac system, which includes the heart), which may not have otherwise been an option for the patient thereby increasing the quality of medical care the patient receives. It will be recognized that the preceding is merely an example of how remote consultation of a patient at a node 109 by a medical service provider at a hub 111 may increase usage of a medical service provider and increase the quality of medical care a patient receives.

Figure 2A:
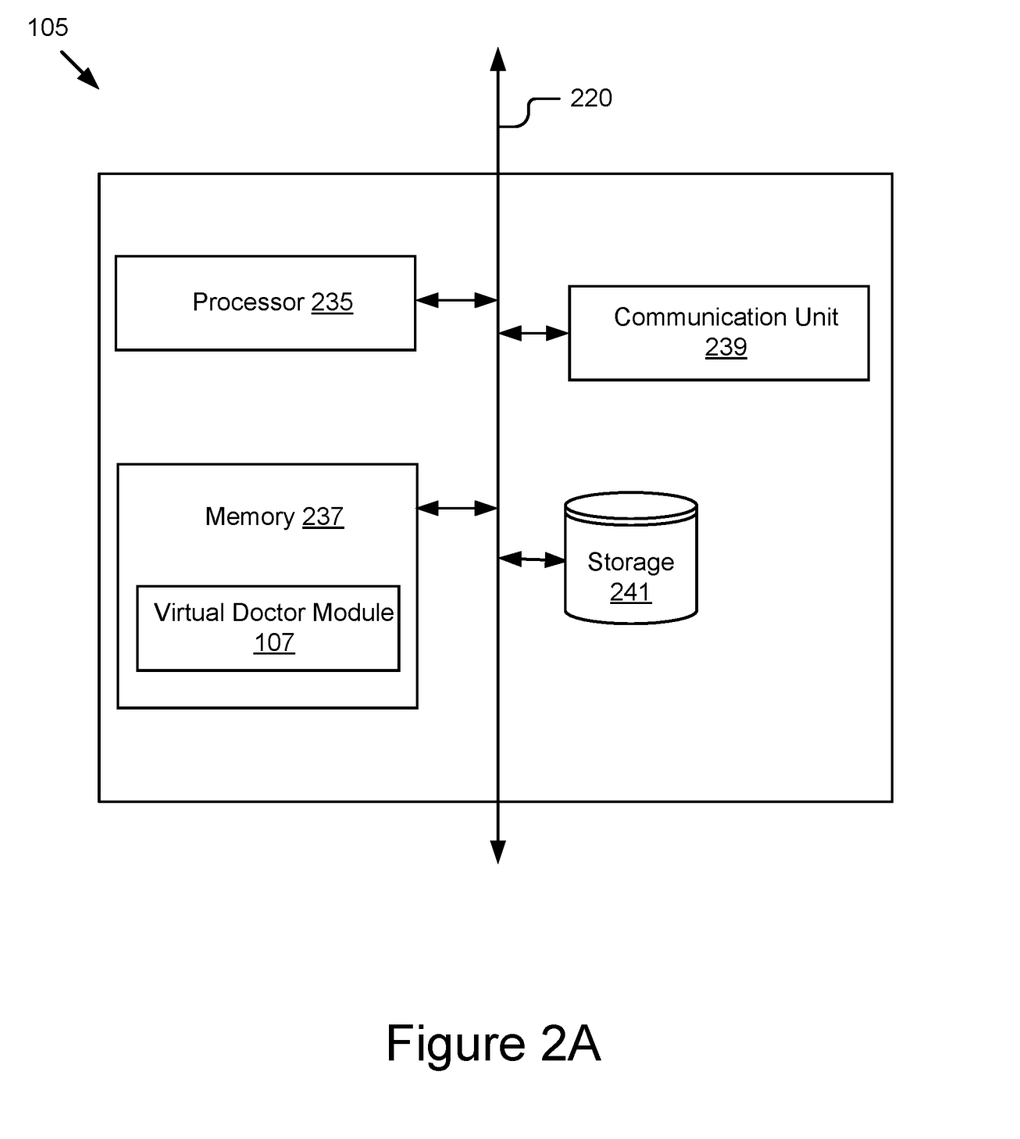
FIG. 2A illustrates a block diagram of a web services server according to one embodiment.

FIG. 2A is a block diagram of a web services server 105 according to one embodiment. As illustrated in FIG. 2A, the web services server 105 includes a processor 235, a memory 237, communications unit 239 and storage 241 coupled to a bus 220. In one embodiment, the functionality of the bus 220 is provided by an interconnecting chipset.

The communication unit 239 receives data from the nodes 109, the hubs 111 and the EMR server 101. The communication unit 239 is coupled to the bus 220. In one embodiment, the communication unit 239 includes a port for direct physical connection to the network 125 or to another communication channel. In another embodiment, the communication unit 239 includes a wireless transceiver for exchanging data with the network 125, or with another communication channel, using one or more wireless communication methods.

The processor 235 may be any general-purpose processor. The processor 235 comprises an arithmetic logic unit, a microprocessor, a general purpose controller or some other processor array to perform computations and execute code and routines. The processor 235 is coupled to the bus 220 for communication with the other components of the web services server 105. Processor 235 processes data signals and may comprise various computing architectures including a complex instruction set computer (CISC) architecture, a reduced instruction set computer (RISC) architecture, or an architecture implementing a combination of instruction sets. Although only a single processor is shown in FIG. 2A, multiple processors may be included. The processing capability may be limited to supporting the display of images and the capture and transmission of images. The processing capability might be enough to perform more complex tasks, including various types of feature extraction and sampling. The web services server 105 also includes an operating system executable by the processor. It will be obvious to one skilled in the art that other processors, operating systems, sensors, displays and physical configurations are possible.

The memory 237 is a non-transitory storage medium. The memory 237 holds instructions and/or data that may be executed by the processor 235. In one embodiment, the instructions and/or data stored on the memory 237 comprise code for performing any and/or all of the techniques described herein. The memory 237 may be a dynamic random access memory (DRAM) device, a static random access memory (SRAM) device, flash memory or some other memory device known in the art. In one embodiment, the memory 237 also includes a non-volatile memory or similar permanent storage device and media, for example, a hard disk drive, a floppy disk drive, a CD-ROM device, a DVD-ROM device, a DVD-RAM device, a DVD-RW device, a flash memory device, or some other mass storage device known in the art for storing information on a more permanent basis. The memory 237 is coupled by the bus 220 for communication with the other components of the web services server 105. In one embodiment, the virtual doctor module 107 is stored in memory 237 and executable by the processor 235.

The virtual doctor module 107 is code and routines executable by the processor 235 for triaging and/or treating patients located at a node 109. In one embodiment, the virtual doctor module 107 is a set of instructions executable by the processor 235. In another embodiment, the virtual doctor module 107 is stored in the memory 237 and is accessible and executable by the processor 235. Details describing the functionality and components of the virtual doctor module 107 are explained in further detail below in reference to FIGS. 2B and 3.

The storage device 241 is any device capable of holding data, for example, a hard drive or a solid-state memory device. The storage device 241 is a non-volatile memory device or similar permanent storage device and media. In one embodiment, the storage device 241 stores data and information of the web services server 105. For example, data and information generated by the virtual doctor module 107 and its components (e.g., a knowledge database for the virtual doctor) may be stored on the storage device 241.

As used herein, the term module refers to computer program logic utilized to provide the specified functionality. Thus, a module can be implemented in hardware, firmware, and/or software. In one embodiment, program modules are stored on the storage device 241, loaded into the memory 237 and executed by the processor 235. Embodiments of the entities described herein can include other and/or different modules than the ones described here. In addition, the functionality attributed to the modules can be performed by other or different modules in other embodiments. Moreover, this description occasionally omits the term module for purposes of clarity and convenience.

Figure 2B:
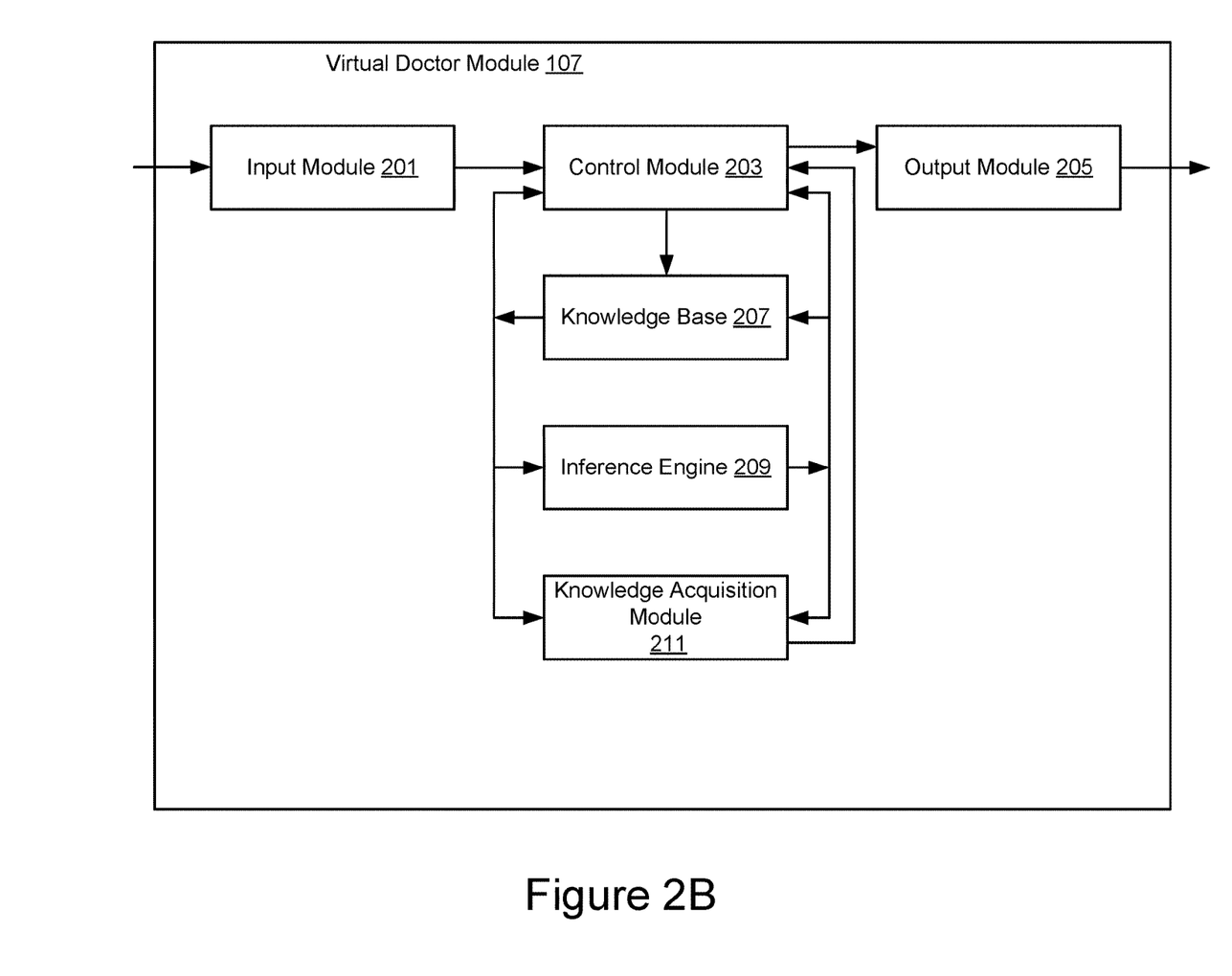
FIG. 2B illustrates a block diagram of a virtual doctor module according to one embodiment.

Referring now to FIG. 2B, illustrates a block diagram of a virtual doctor module 107 according to one embodiment. In one embodiment, the virtual doctor module includes an input module 201, a control module 203, an output module 205, a knowledge base 207, an inference engine 209, and a knowledge acquisition module 211.

It will be recognized that the modules comprising the virtual doctor module 107 are not necessarily all on the same web services server 105. In one embodiment, the modules may be distributed across the system 100. For example, in one embodiment, the some or all of the modules may be instantiated at the node 109 or hub 111 and the remaining modules may be instantiated at the web services server 105. In another example, the system may include a second web services server (not shown) and the modules are divided between the two web services servers. This may be particularly advantageous in circumstances where network connectivity between the node 109, the hub 111, and the web services module 105 does not allow for sufficient data to be passed between them.

In one embodiment, a distributed module may be hierarchical such that a smaller portion or version of a module may be resident on a remote device (e.g., at node 109 or hub 111) with a larger main component resident on a central server such as web services server 105. For example, a smaller, local knowledge base may be resident on a computing device or local server at node 109 and a complete knowledge base 207 may be resident on the web services server 105. The virtual doctor module 207 may first query the local knowledge base and resort to a query to the knowledge base resident on the web services module 105 if the local knowledge base does not contain sufficient data to satisfy the query. In some embodiments, this remote query is transparent to the user at the node 109.

In another embodiment, distributed versions of the virtual doctor module 107 may also follow a tiered hierarchical structure. For example, the virtual doctor module 107 resident on web services server 105 may include a very large knowledge base 207 and be run on powerful computing architecture. This type of a virtual doctor module 107 may not be practical or cost-effective to implement in the majority of cases (particularly where Internet connectivity is limited). Further, the large knowledge base 207 may not be necessary to treat the minor medical symptoms typically encountered in a telemedicine environment. For that reason, a virtual doctor module 107 with more limited capabilities (e.g., a smaller knowledge base that is tailored to a local region, demographic, medical specialty, or the like) may be deployed at various locations (local or remote to the node 109) to deal with routine medical cases. In some embodiments, one of these smaller virtual doctor modules 107 may escalate a case to the larger, more capable virtual doctor module 107. In other embodiments, the decision of which virtual doctor module (e.g., a small or large virtual doctor module) to query may be based on other signals (e.g., initial patient input, insurance willingness to pay, patient cost sensitivity, etc.).

The input module 201 may be connected to various input devices and receive signals used by the virtual doctor module 107 to make triage and/or treatment decisions. The input devices may be, for example, a keyboard, a mouse, a touch panel, medical devices, a microphone, a camera, or the like. Similarly, the input may be received from a database or other system, for example, data may be received from the EMR server 101 to be processed by the virtual doctor module 107. In some embodiments, the input module 201 may receive input from wearable devices worn by patients of the telemedicine system.

Wearable devices may be, for example, in the form of commonly used personal items such as watches, bracelets, rings, etc. In other embodiments, wearables may be integrated into articles of clothing worn by the patient. Further, temporary wearables such as patches or devices that are mounted to the body using straps or the like may also provide data to the input module. The general health-related purposes of such wearables are for the monitoring and recording of various vital signs on an on-going bases, to enable the wearer to be pro-active in the management of their health and wellness. Additionally, by providing this data to the input module of the virtual doctor 107, the virtual doctor can more effectively diagnose and treat medical conditions or emergencies experienced by the patient regardless of where the patient may be located. This is in contrast to the current healthcare system relies on discrete sets of information about a patient when the patient arrive at a point of care for treatment. Having the data from wearables, the virtual doctor 107 can provide greater continuity and quality of care at lower cost.

The control module 203 is code and/or routines for operating the virtual doctor module 107. The control module 203, for example, provides control for input, output, and processing functions provided by the virtual doctor module 107. The control module 203 may also provide a user interface and/or console for physicians and node personnel. For example, the control module 203 may provide a user interface for a physician or other medical service provider at a remote operations or control center to monitor the decisions of the virtual doctor for multiple patients and intervene if the situation warrants.

The output module 205 is code and/or routines to provide an output of the virtual doctor module 107. For example the output module 205 may provide a user interface or information to the patient at the node 109. In various embodiments, the output module 205 may include a speech synthesis module to provide spoken communication to a patient. The speech synthesis module may include options for controlling the age, gender, or accent of the synthesized voice to maximize patient comfort. The output module 205, in some embodiments, may provide a computer-generated avatar of a virtual doctor for display to the patient at the node 109. The computer-generated avatar may similarly be customized by age, gender, ethnicity, or the like. The output module 205 may be connected to the EMR server 101 or other library medical imagery to provide playback of images and/or video to the patient at the node 109 or the medical professional at the hub 111. In some embodiments, in addition to or in lieu of spoken communication, the output module 205 may provide closed caption text to be presented to the patient at the node 109 or the medical professional at the hub 111.

The knowledge base 207 may be known public or proprietary technology used to store the information used by the inference engine 209 to perform triage, diagnosis, and/or treatment operations as disclosed herein. In some embodiments, the information may be stored using a flat structure or a hierarchical object based structure. The knowledge base 207 may be constantly updated based on input from the knowledge acquisition module 211 and the inference engine 209. The knowledge base 207 may include clinical protocols and other information for the inference engine 209 to use in determining a course of action as described below.

The inference engine 209 may be any public or proprietary rules based engine for determining a course of action based on the knowledge base 207 and signals from the input module 201. In some embodiments, the inference engine 209 may also rely on signals and data received from health tracking applications and/or devices associated with a patient. In some embodiments, the inference engine may use forward chaining with performance improvement options such as the use of magic sets.

The knowledge acquisition module 211 may update the knowledge base 207, via control module 203, using signals from the input module 201, the knowledge base 207, and the inference engine 209. In one embodiment, the knowledge acquisition module 211 may use machine learning techniques to improve the performance of the knowledge base 207 and inference engine 209. The machine learning techniques may include, for example, supervised learning, unsupervised learning, reinforced learning, or other public or proprietary learning techniques. In some embodiments, the knowledge acquisition module 211 may include mechanisms for manual or remote input from experts outside of the virtual doctor module 107. For example, physicians and/or system administrators may provide signals directly (not shown) to the knowledge acquisition module 211 to update the knowledge base 207 and/or the inference engine 209. In other examples, the physicians and/or system administrators may provide signals to update the knowledge acquisition module 211 and/or the inference engine 209 via the input module 201 and/or control module 203. In some embodiments, the knowledge acquisition module 211 may provide training protocols that can be run in conjunction with test patients to measure the performance of the virtual doctor module 107.

Figure 3:
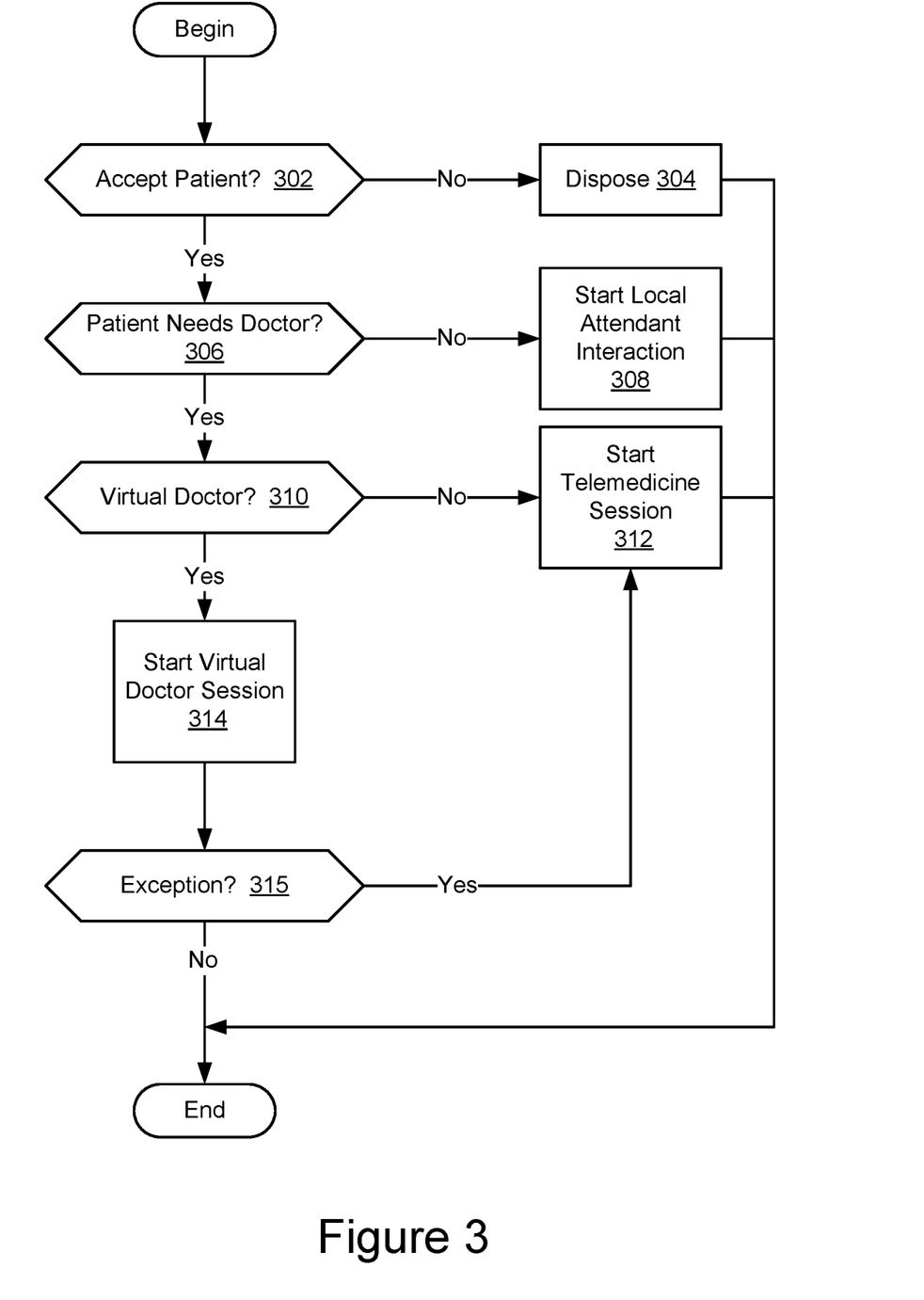
FIG. 3 illustrates a flow chart of an example workflow for operating an advanced telemedicine system with a virtual doctor according to one embodiment.

FIG. 3 is a flow chart illustrating an example workflow for operating an advanced telemedicine system 100 with virtual doctor 107 according to one embodiment. The process begins at 302 by determining whether to accept a patient at the node 109. For example, an attendant at the node 109 may greet the patient and input initial information regarding the patient and/or the patient's symptoms/condition. The inference engine 209 may evaluate the patient using the data input at the node 109, or other data gathered by the virtual doctor module 107, using clinical protocols in the knowledge base 207. If the inference engine 209 determines that the patient should not be accepted, at 304 the case is disposed. For example, the inference engine 209 may determine based on inputs from the node 109 (e.g., information input by the attendant, information from medical devices, etc.) that the patient's condition is critical and requires emergency attention. The node attendant may be alerted and emergency medical services contacted. In another example, the patient may not be accepted if the requested service is not included in a services provided by the telemedicine system 100 (e.g., the patient wants grief counseling, the patient has a skin problem and there are no dermatologists available at the hub, etc.).

If the virtual doctor 107 determines to accept the patient, then the virtual doctor 107 determines at 306 whether the patient needs to see a doctor. Similar to the initial assessment, the inference engine 209 may make the determination at 306 based on inputs from the node 109 and the knowledge base 207. If, at 306, the inference engine 209 determines that the patient does not need to see a doctor, the virtual doctor 107 initiates an interaction at 308 with the local attendant. For example, if the patient's condition is minor and can by treated by the node attendant (e.g., a nurse, nurse practitioner, physician's assistant, or the like) the virtual doctor may provide a notification to the patient and/or node attendant.

At 310, if the inference engine 209 determines that the patient needs to see a doctor at 306, the inference engine 209 determines whether the patient can be treated by a virtual doctor. The inference engine 209 may use input from the node 109 and the knowledge base 207 to determine whether the patient can be seen by a virtual doctor. In some embodiments, an informed consent interface is provided to the patient to inform the patient that he/she is accepting diagnosis and/or treatment advice from a virtual doctor. Further, the inference engine 209 and knowledge base 207 may be programmed with a risk assessment protocol to determine whether there is significant risk in evaluating the patient using the virtual doctor. For example, a risk level 1 to 5 (with 1 being high risk and 5 being low risk) may be assigned to each patient based on inputs at the node 109 and only low risk patients (e.g., risk level 4 and 5) may be accepted.

If, at 310, the inference engine 209 determines that the patient is not a candidate for virtual doctor treatment (e.g., the patient does not consent, inputs are not suitable for virtual doctor, the risk is too high, etc.), the system 100 may initiate a telemedicine session 312. In some embodiments, the patient is put in a queue to see a live doctor via a telemedicine session.

If the inference engine 209 determines that the patient is a candidate for treatment by the virtual doctor, at 314 the system initiates a virtual doctor session. The virtual doctor session may be initiated by providing a virtual doctor avatar on a display device at the node and providing instructions to the patient for interacting with the virtual doctor. In some embodiments, one or more virtual doctor sessions may be monitored by a medical professional at a remote control or operations center. When an exception is noted by the medical professional, at 315, the medical professional may intervene when/if necessary to maintain a standard of care for the patient. In some embodiments, the monitoring module 119 may provide a dashboard to the medical professional to monitor the virtual doctor sessions. After a case is disposed at 304, an interaction with the local attendant has been started at 308, a telemedicine session has been started at 312, or no exception has been noted at 315, the session ends.

The foregoing description of the embodiments has been presented for the purposes of illustration and description. It is not intended to be exhaustive or to limit the present embodiments to the precise forms disclosed. Many modifications and variations are possible in light of the above teaching. It is intended that the scope of the present embodiments be limited not by this detailed description, but rather by the claims of this application. As will be understood by those familiar with the art, the present embodiments may take other specific forms without departing from the spirit or essential characteristics thereof. Likewise, the particular naming and division of the modules, routines, features, attributes, methodologies and other aspects are not mandatory or significant, and the mechanisms that implement one embodiment or its features may have different names, divisions and/or formats. Furthermore, as will be apparent, the modules, routines, features, attributes, methodologies and other aspects of the embodiments can be implemented as software, hardware, firmware or any combination of the three. Also, wherever a component, an example of which is a module, is implemented as software, the component can be implemented as a standalone program, as part of a larger program, as a plurality of separate programs, as a statically or dynamically linked library, as a kernel loadable module, as a device driver, and/or in every and any other way known now or in the future. Additionally, the embodiments are in no way limited to implementation in any specific programming language, or for any specific operating system or environment. Accordingly, the disclosure is intended to be illustrative, but not limiting, of the scope, which is set forth in the following claims.

What is claimed is:

1. A method comprising:
receiving a registration of a patient;
receiving an input regarding the patient;
selecting, based on the input, a first virtual doctor artificial intelligence system with a first knowledge base of a first size;
determining whether the patient can be treated by a first virtual doctor of the first virtual doctor artificial intelligence system based on querying the first knowledge base of the first size;
determining whether the patient can be treated by a second virtual doctor of a second virtual doctor artificial intelligence system, the second virtual doctor artificial intelligence system being associated with a second knowledge base of a second size;
providing a treatment decision for the patient, using an inference engine and the first knowledge base of the first virtual doctor, based on the input and responsive to determining that the patient can be treated by the first virtual doctor of the first virtual doctor artificial intelligence system;
providing the treatment decision for the patient, using the inference engine and the second knowledge base of the second virtual doctor, based on the input and responsive to determining that the patient can be treated by the second virtual doctor of the second virtual doctor artificial intelligence system; and
determining that the patient cannot be treated by either the first virtual doctor or the second virtual doctor;
placing the patient in a queue of a telemedicine session for treatment by a live healthcare professional responsive to determining that the patient cannot be treated by either the first virtual doctor or the second virtual doctor; and
causing transmission of the input regarding the patient to be activated to transmit the input regarding the patient to the live healthcare professional when there is a direct connectivity to the live healthcare professional.

2. The method of claim 1, wherein the input is received from a medical device at a location of the patient.

3. The method of claim 1, wherein providing the treatment decision for the patient comprises:
receiving data from a wearable device of the patient; and
analyzing, using the inference engine and one of the first knowledge base and the second knowledge base, the data from the wearable device of the patient and the input to determine the treatment decision.

4. The method of claim 1 further comprising:
monitoring treatment of the patient by the first or second virtual doctor; and
placing the patient in a queue for treatment by the live healthcare professional in response to identifying an exception with the treatment of the patient by the first or second virtual doctor.

5. The method of claim 1, further comprising transmitting a synthesized voice prompt for presentation to the patient, wherein the synthesized voice prompt represents the first or second virtual doctor and includes one or more of a question and the treatment decision for the patient.

6. The method of claim 1, further comprising transmitting a computer generated avatar for presentation to the patient, wherein the computer generated avatar represents the first or second virtual doctor and presents one or more of a question and the treatment decision for the patient to the patient.

7. The method of claim 1, further comprising updating a patient medical record associated with the patient with the treatment decision.

8. A system comprising:
one or more processors; and
a memory storing instructions, which when executed cause the one or more processors to:
receive a registration of a patient;
receive an input regarding the patient;
select, based on the input, a first virtual doctor artificial intelligence system with a first knowledge base of a first size;
determine whether the patient can be treated by a first virtual doctor of the first virtual doctor artificial intelligence system based on querying the first knowledge base of the first size;
determine whether the patient can be treated by a second virtual doctor of a second virtual doctor artificial intelligence system, the second virtual doctor artificial intelligence system being associated with a second knowledge base of a second size;
provide a treatment decision for the patient, using an inference engine and the first knowledge base of the first virtual doctor, based on the input and responsive to determining that the patient can be treated by the first virtual doctor of the first virtual doctor artificial intelligence system;
provide the treatment decision for the patient, using the inference engine and the second knowledge base of the second virtual doctor, based on the input and responsive to determining that the patient can be treated by the second virtual doctor of the second virtual doctor artificial intelligence system; and
determine that the patient cannot be treated by either the first virtual doctor or the second virtual doctor;
place the patient in a queue of a telemedicine session for treatment by a live healthcare professional responsive to determining that the patient cannot be treated by either the first virtual doctor or the second virtual doctor; and
cause transmission of the input regarding the patient to be activated to transmit the input regarding the patient to the live healthcare professional when there is a direct connectivity to the live healthcare professional.

9. The system of claim 8, wherein the input is received from a medical device at a location of the patient.

10. The system of claim 8, wherein to provide the treatment decision for the patient, the instructions cause the one or more processors to:
receive data from a wearable device of the patient; and
analyze, using the inference engine and one of the first knowledge base and the second knowledge base, the data from the wearable device of the patient and the input to determine the treatment decision.

11. The system of claim 8, wherein the instructions cause the one or more processors to:
monitor treatment of the patient by the first or second virtual doctor; and place the patient in a queue for treatment by the live healthcare professional in response to identifying an exception with the treatment of the patient by the first or second virtual doctor.

12. The system of claim 8, wherein the instructions cause the one or more processors to transmit a synthesized voice prompt for presentation to the patient, wherein the synthesized voice prompt represents the first or second virtual doctor and includes one or more of a question and the treatment decision for the patient.

13. The system of claim 8, wherein the instructions cause the one or more processors to transmit a computer generated avatar for presentation to the patient, wherein the computer generated avatar represents the first or second virtual doctor and presents one or more of a question and the treatment decision for the patient to the patient.

14. The system of claim 8, wherein the instructions cause the one or more processors to update a patient medical record associated with the patient with the treatment decision.

15. A non-transitory computer readable medium storing instructions which, when executed by a computer, cause the computer to:
receive a registration of a patient;
receive an input regarding the patient;
select, based on the input, a first virtual doctor artificial intelligence system with a first knowledge base of a first size;
determine, using the input, whether the patient can be treated by a first virtual doctor of the first virtual doctor artificial intelligence system based on querying the first knowledge base of the first size;
determine whether the patient can be treated by a second virtual doctor of a second virtual doctor artificial intelligence system, the second virtual doctor artificial intelligence system being associated with a second knowledge base of a second size;
provide a treatment decision for the patient, using an inference engine and the first knowledge base of the first virtual doctor, based on the input and responsive to determining that the patient can be treated by the first virtual doctor of the first virtual doctor artificial intelligence system;
provide the treatment decision for the patient, using the inference engine and the second knowledge base of the second virtual doctor, based on the input and responsive to determining that the patient can be treated by the second virtual doctor of the second virtual doctor artificial intelligence system; and
determine that the patient cannot be treated by either the first virtual doctor or the second virtual doctor;
place the patient in a queue of a telemedicine session for treatment by a live healthcare professional responsive to determining that the patient cannot be treated by either the first virtual doctor or the second virtual doctor; and
cause transmission of the input regarding the patient to be activated to transmit the input regarding the patient to the live healthcare professional when there is a direct connectivity to the live healthcare professional.

16. The non-transitory computer readable medium of claim 15, wherein the input is received from a medical device at a location of the patient.

17. The non-transitory computer readable medium of claim 15, wherein to provide the treatment decision for the patient, the instructions cause the computer to:
receive data from a wearable device of the patient; and
analyze, using the inference engine and one of the first knowledge base and the second knowledge base, the data from the wearable device of the patient and the input to determine the treatment decision.

18. The non-transitory computer readable medium of claim 15, wherein the instructions cause the computer to:
monitor treatment of the patient by the first or second virtual doctor; and
place the patient in a queue for treatment by the live healthcare professional in response to identifying an exception with the treatment of the patient by the first or second virtual doctor.

19. The non-transitory computer readable medium of claim 15, wherein the instructions cause the computer to transmit a synthesized voice prompt for presentation to the patient, wherein the synthesized voice prompt represents the first or second virtual doctor and includes one or more of a question and the treatment decision for the patient.

20. The non-transitory computer readable medium of claim 15, wherein the instructions cause the computer to transmit a computer generated avatar for presentation to the patient, wherein the computer generated avatar represents the first or second virtual doctor and presents one or more of a question and the treatment decision for the patient to the patient.

* * * * *